United States Patent [19]
Corneau

[11] 3,955,425
[45] May 11, 1976

[54] PIPE WALL THICKNESS GAUGE

[75] Inventor: George E. Corneau, Central Falls, R.I.

[73] Assignee: Indev, Inc., Pawtucket, R.I.

[22] Filed: Aug. 16, 1974

[21] Appl. No.: 497,947

[52] U.S. Cl. ............................... 73/552; 73/67.8 S
[51] Int. Cl.² ......................................... G01N 29/00
[58] Field of Search ............ 73/552, 67.8 S, 67.8 R, 73/67.7, 71.5 US; 324/37

[56] References Cited
UNITED STATES PATENTS

| | | | |
|---|---|---|---|
| 3,248,933 | 5/1966 | Stebbins | 73/67.8 S X |
| 3,415,111 | 12/1968 | Chattaway et al. | 73/71.5 US X |
| 3,533,281 | 10/1970 | Hetherington | 73/71.5 US |
| 3,540,266 | 11/1970 | Lofgren | 73/67.8 S |
| 3,582,771 | 6/1971 | Placke | 73/71.5 US X |
| 3,612,987 | 10/1971 | Placke | 324/37 |
| 3,640,123 | 2/1972 | Vogt et al. | 73/67.8 |
| 3,827,287 | 8/1974 | Boggs et al. | 73/67.8 S |

Primary Examiner—Richard C. Queisser
Assistant Examiner—Stephen A. Kreitman

[57] ABSTRACT

A pipe wall thickness gauge including an acoustic signal generator and sensor in a housing mounted in a base adapted for underwater use and continuous monitoring of the wall thickness of a pipe, such as freshly extruded plastic pipe. The gauge includes a base adapted to surround the pipe, the base consisting of at least two base sections each having at least one pipe positioning member with pipe centering elements at the tip thereof; at least one of the pipe positioning members including a mounting means for the housing of the acoustic signal generator and sensor. Preferably, adjusting means are included to move the pipe positioning member inwardly or outwardly to accomodate different diameter pipes and to vary, within limits, the position and direction of the acoustic signal generator and sensor. Various other features are included in the preferred form of the present invention.

1 Claim, 10 Drawing Figures

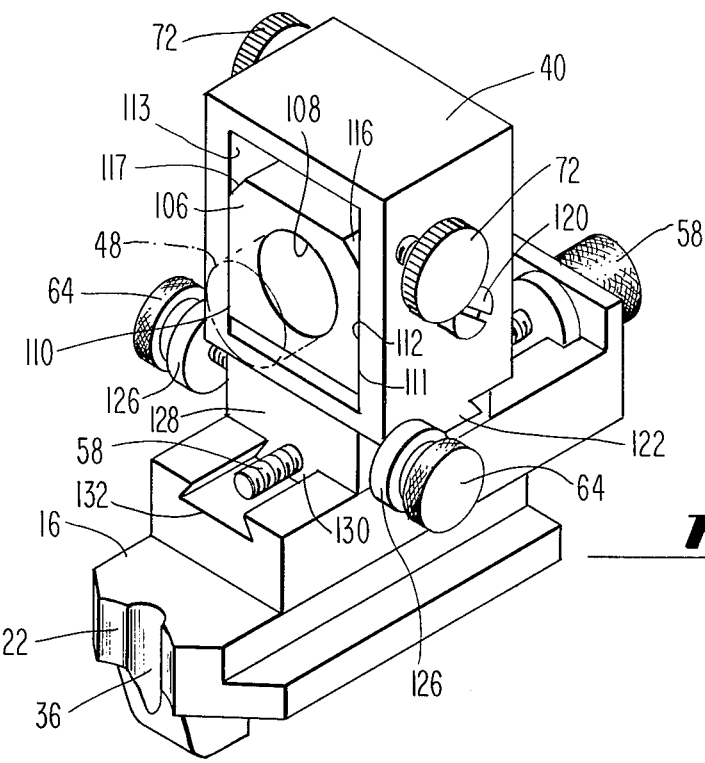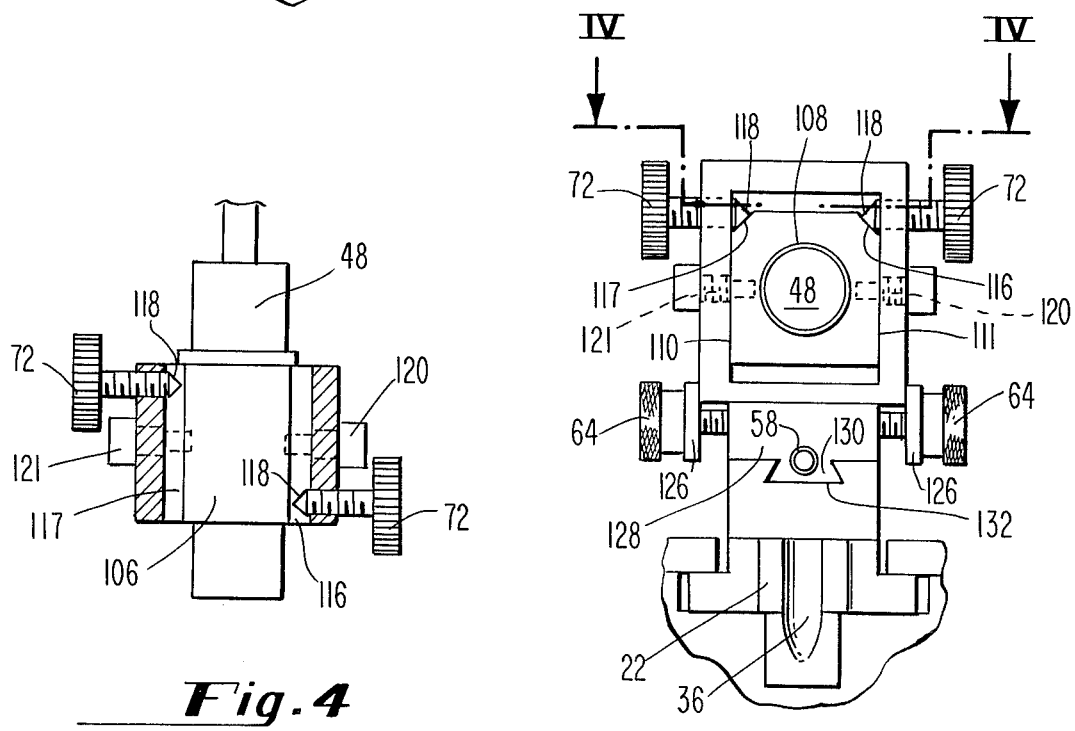

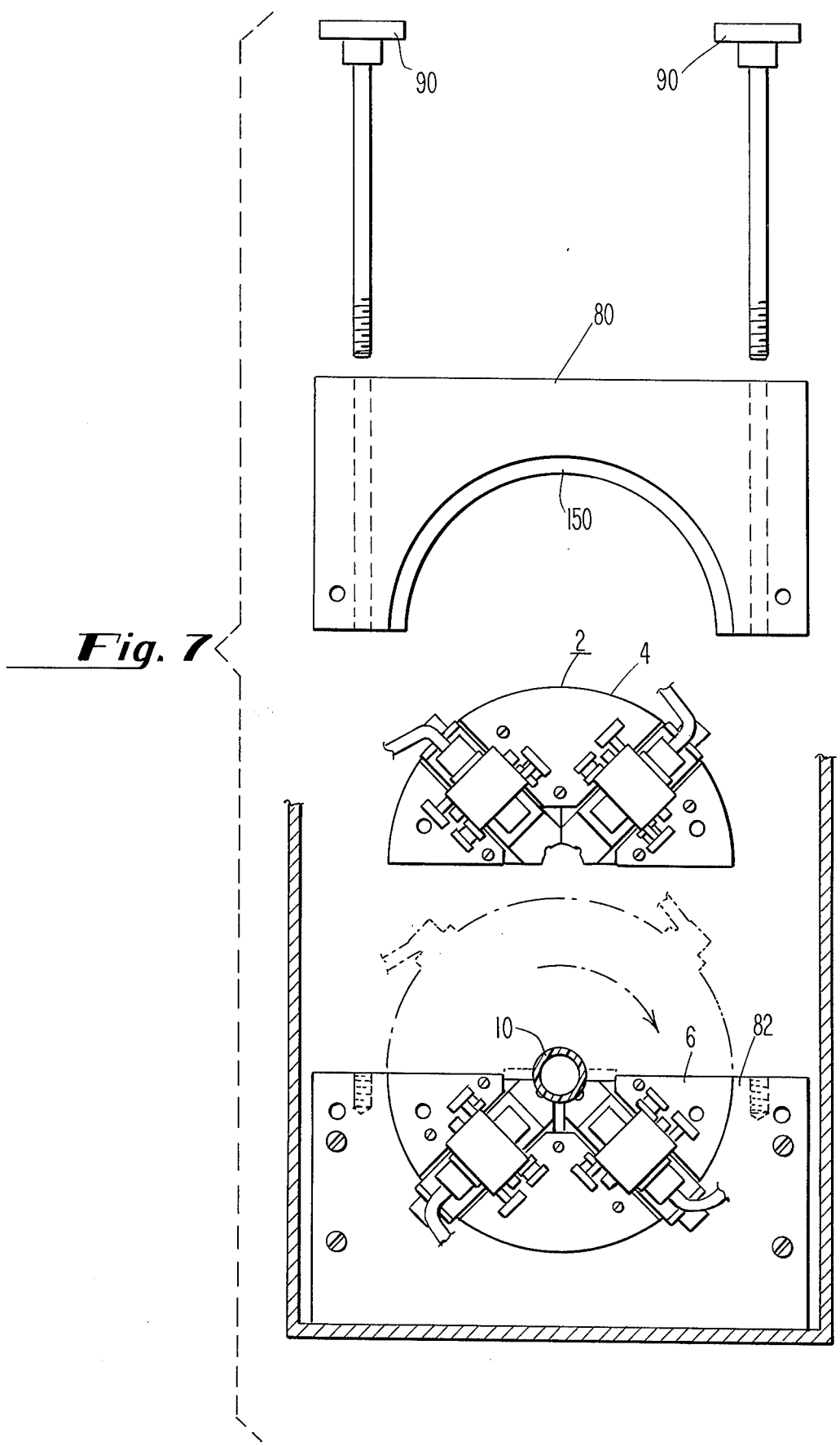

PIPE WALL THICKNESS GAUGE

This invention pertains to a pipe wall thickness gauge and particularly to such a gauge adapted to monitor the wall thickness of a plastic pipe as it is extruded into a water bath.

A variety of means have been devised for measuring the wall thickness of pipes of various types.

In one type of prior art pipe wall thickness gauge intended specifically for the monitoring of the wall thickness of a plastic pipe as it is extruded into a water bath, an acoustic signal generator and sensor, located in the water bath near the pipe, is associated with supporting means at the surface of the water bath. In this device, precise positioning of the acoustic generator-sensor, relative to the pipe, is difficult. Such devices are generally awkward to use and unreliable.

It is therefore an object of the present invention to provide a pipe wall thickness gauge wherein the relative position of the pipe to the gauge is automatically maintained.

A further object of this invention is to provide such a gauge which is easily adjustable to accomodate a range of pipe diameters.

Still another object of this invention is to provide such a gauge which is conveniently adjustable to permit precise positioning of the acoustic generator-sensor relative to the pipe.

A still further object of this invention is to provide a pipe wall thickness gauge which may be easily rotated about the pipe to sense the pipe wall thickness at different points on the circumference of the pipe.

One further object of the invention is to provide a pipe wall thickness gauge adapted to monitor continuously pipe wall thickness at several points around the circumference of the pipe on a continuous basis as the pipe passes through the gauge.

These and other objects, which will be apparent in the course of the subsequent description, are met, briefly, by a pipe wall thickness gauge consisting of a gauge base adapted to surround circumferentially a pipe located along the axis of the gauge, the base consisting of at least two separable sectors, each of the sectors including at least one pipe positioning member with pipe centering elements at the tips thereof pointed radially inward toward the axis of the gauge. One of the pipe positioning members also includes means for holding an acoustic signal generator-sensor housing so that the generator-sensor located therein is precisely positioned with respect to a pipe centered within the pipe centering elements of the positioning members mounted on the gauge base.

Preferably, the gauge base consists of two sectors, each subtending arcs of 180° about the gauge base sectors, each including two pipe positioning members, all of the pipe positioning members being angularly displaced 90° from adjacent members. Inwardly directed concave centering elements at the tips of the positioning members are radially adjustable to accomodate different pipe sizes and two of the pipe positioning members may be slightly movable in a radial direction and urged inwardly in order automatically to maintain the pipe in a central position along the axis of the gauge notwithstanding slight irregularities or eccentricities in a pipe as it passes through the gauge in a continuous fashion. Preferably also, the generator-sensor housing holder is adjustable so that its position may be moved radially (closer to or away from a pipe centered in the gauge) or transversely thereof or angularly inclined with respect to a plane perpendicular to the axis of the gauge. The invention may be better understood by reference to the following detailed description taken in conjunction with the subjoined claims and the appended drawings, in which:

FIG. 3 is a detailed view of one part of the gauge shown in FIGS. 1 and 2, that part being viewed as seen in the plane 3—3 of FIG. 2;

FIG. 4 is a partial sectional view of that part of the gauge shown in FIG. 3 taken in the plane 4—4 of FIG. 3;

FIG. 5 is a perspective view of the same part of the gauge shown in FIGS. 3 and 4, particularly including a pipe positioning member and the centering element or tip thereof and the holder and retaining means for the acoustic signal generator and receiver;

FIG. 7 is a disassembled view of various parts of the gauge shown in FIG. 1;

Figure 1:
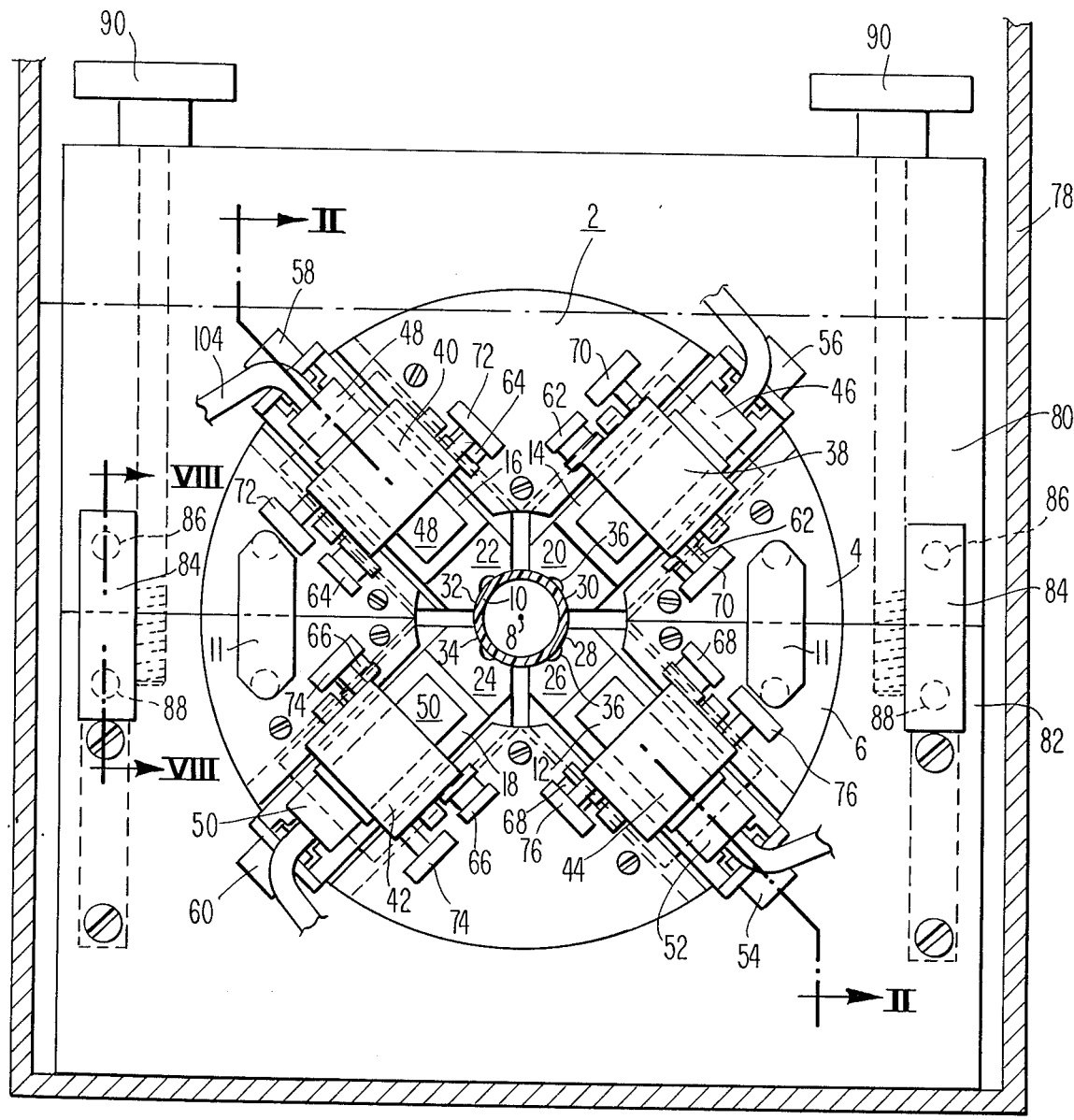
FIG. 1 is an elevation view of a preferred pipe wall thickness gauge of the present invention mounted for use in a water bath and with a pipe passing therethrough, the water bath and the pipe being shown in section.
Figure 10:
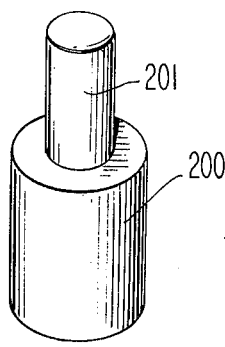
Figure 9:
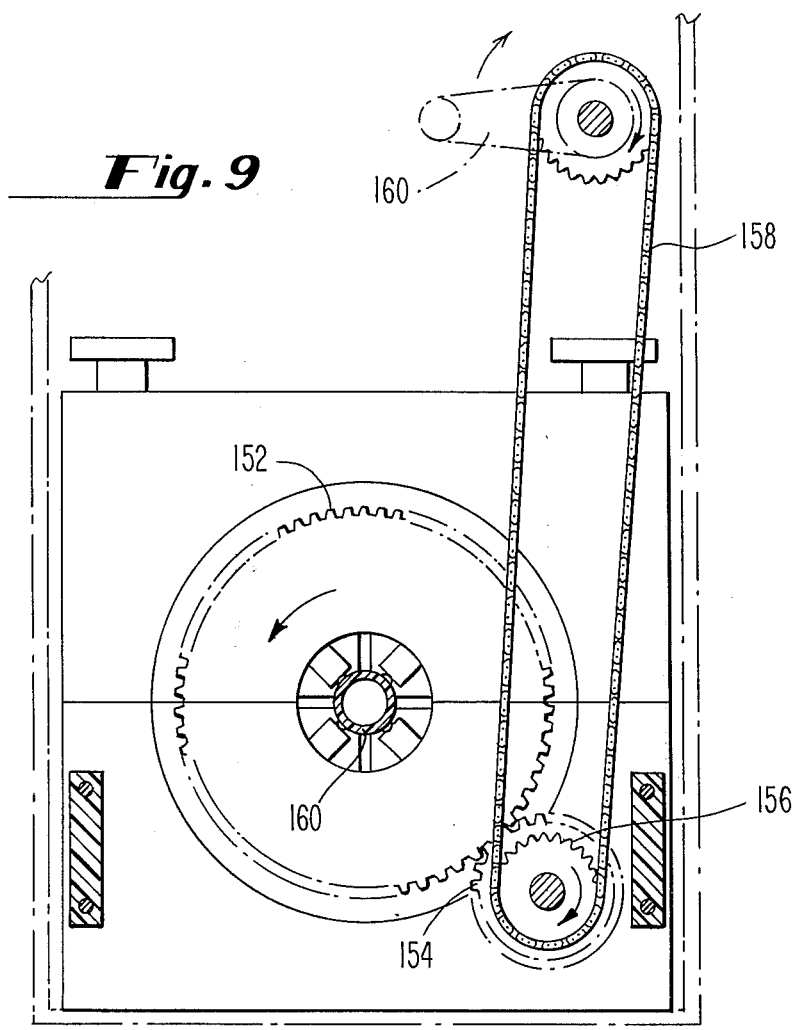

FIG. 9 is a schematic view of an embodiment of the invention including means for rotating the gauge about a pipe; and FIG. 10 is a schematic view of an embodiment of the invention utilizing a pre-setting chuck. Turning more specifically to FIG. 1, there is shown a preferred embodiment of the pipe wall thickness gauge of the present invention. Gauge 2 includes base sectors 4 and 6 which, each subtending an arc of 180° about the axis 8 of the gauge, together surround circumferentially a pipe 10 the wall thickness of which is to be measured. Base sectors 4 and 6 are secured together by fastening pins 11 projecting into holes provided therefor in base sectors 4 and 6. Pipe positioning members 12, 14, 16 and 18 are mounted in channels provided therefor in base sectors 4 and 6 with pipe centering elements 20, 22, 24 and 26 at the tips thereof directed inward radially toward axis 8. Concave surfaces 28, 30, 32 and 34 assist in the centering of pipe 10 while indentations 36 facilitate rotation of gauge 2 about pipe 10 by reducing friction between pipe 10 and the centering elements.

Mounted within holders 38, 40, 42 and 44 are acoustic signal generator and receiver housings 46, 48, 50 and 52. Holders 38–44 each include radial position adjustment screws 54, 56, 58 and 60, transverse position adjustment screws 62, 64, 66 and 68 and sensor inclination adjustment screw pairs 70, 72, 74 and 76.

Figure 8:
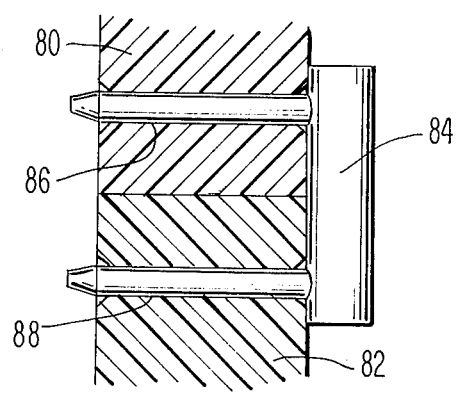
FIG. 8 is a partial sectional view exploded to show the means of attachment of the sections of gauge base mount shown in FIG. 1.

Gauge 2, as ordinarily used for sensing the wall thickness of a plastic pipe as it is extruded into a water bath, is shown in FIG. 1 in such a water bath enclosed in a trough 78 with a gauge mount fixed therein consisting of an upper half 80 and a lower half 82 pinned together by pin 84 projecting into holes 86 and 88 provided therefor in gauge mount halves 80 and 82, all as better seen in the detailed sectional view of FIG. 8.

As in the case of fastening pin 11 holding together base sectors 4 and 6, the pin is merely friction fit into these holes for easy disassembly of the gauge mount halves.

Extended shaft bolts 90 are also used to fasten together upper half 80 and lower half 82 of the gauge mount.

Figure 2:
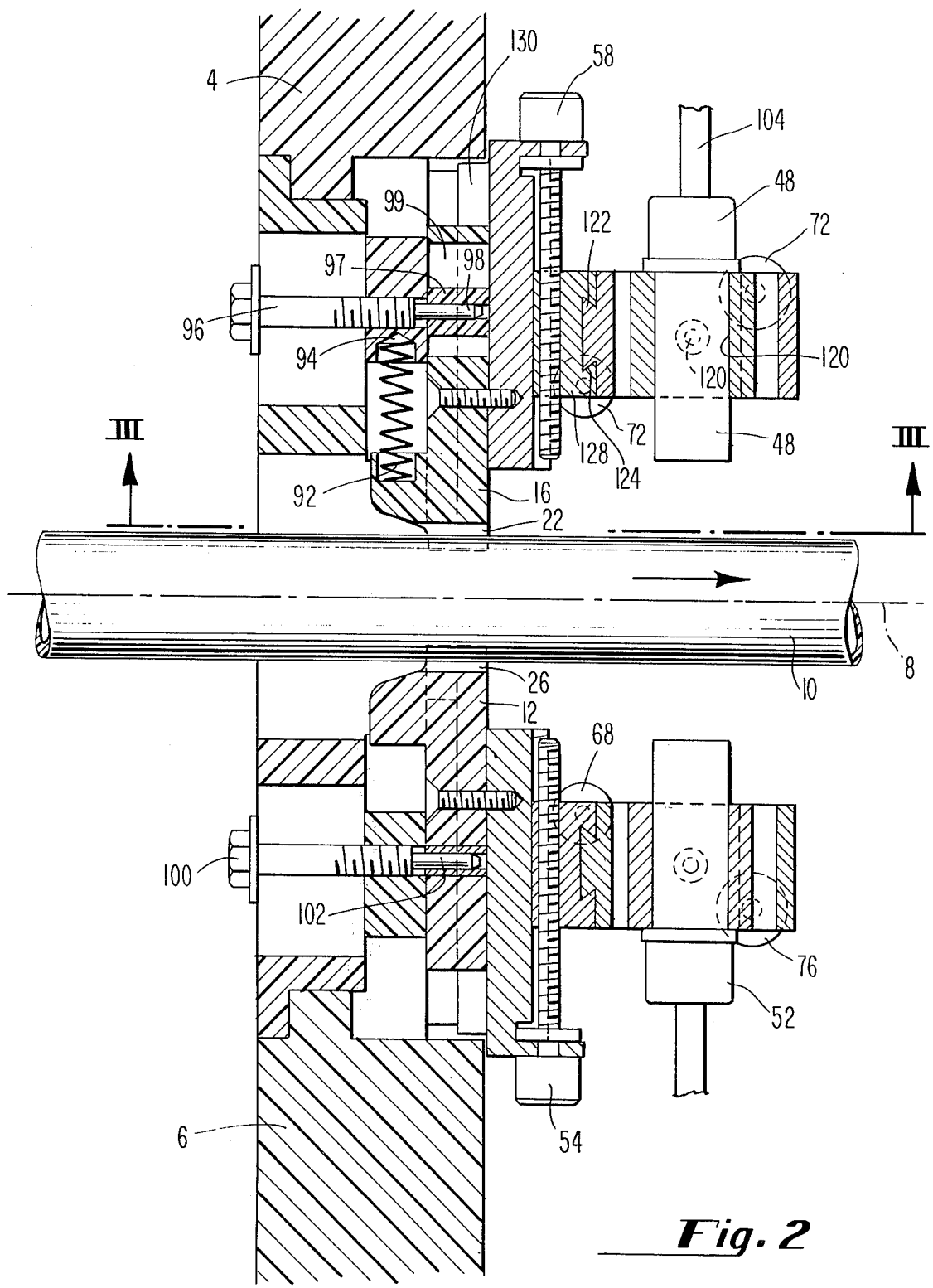
FIG. 2 is a sectional view in the plane 2—2 of the gauge shown in FIG. 1.

In FIG. 2, pipe positioning member 16 is seen to have slight freedom for movement in the radial direction (i.e., the direction toward axis 8) and is urged toward pipe 10 by spring biasing means 92 acting against spring retainer 94 bolted to base sector 4 by bolt 96 having a pivot axis extension 98 about which pipe positioning member 16 has slight freedom of movement in a plane perpendicular to axis 8. In a similar manner, pipe positioning member 12 is fastened to base sector 6 by bolt 100 having pivot extension 102. Member 12, however, is fixed in its radial position by bolt 100 while member 16 is free to move by virtue of slot 99 in the base of member 16 in which is fitted pivot retainer 97.

In this embodiment of the invention, two of the pipe positioning members 12 and 18 are fixed radially, while two others 16 and 14 are spring biased in the radial direction to assist in centering pipe 10 within pipe centering elements 20, 22, 24 and 26. All of the pipe positioning members are pivoted for slight movement in the plane perpendicular to axis 8 also to assist in maintaining pipe 10 centered within the pipe centering elements, particularly to permit slight unevenness or eccentricity in pipe 10.

Also seen in FIG. 2 is the acoustic signal generator-sensor housing 48 and electrical lead lines 104 to an electronic signal timing and indicator means, not shown, for causing the acoustic generator in housing 48 to emit a signal and causing the sensor in housing 48 to receive successive reflections of that signal from the inside and outside of the wall of pipe 10 and then to convert the time delay between the two reflections into an indication of pipe wall thickness.

As best seen in FIGS. 3–5, acoustic signal generator-sensor housing 48 is mounted on pipe positioning member 16 with several adjustment means for controlling precisely the position and direction of pointing of acoustic signal generator-sensor housing 48. More specifically, there is provided a retainer 106 with a hole 108 for housing 48 (shown in phantom FIG. 5). Retainer 106 includes flat side walls 110 and 111 mating with flat side walls 112 and 113 of holder 40. Flat side walls 110 and 111 of retainer 106 are adjacent flat surfaces 116 and 117 forming angles therewith. Sensor inclination adjustment screw 72 at different radial positions along retainer 106 are threaded for adjustment in holder 40 with camming tips 118 (seen best in FIG. 3) in contact with angle forming flat surfaces 116 and 117.

About midway along mounting hole 108 for the acoustic signal generator-sensor housing and on either side of that housing hole are provided pivotal connections 120 and 121 through the side walls of holder 40 and retainer 106. Holder 40 is further mounted with a transversely sliding base 122 in a mating channel. Transverse adjustment screws 64 on a common transverse axis include expanded heads 126 in contact with the lower portion of the outer side walls of holder 40. Adjustment of screws 64 thereby permits transverse adjustment of position of holder 40 and therefore of acoustic signal generator-sensor housing 48. Radial positioning adjustment is similarly controlled by adjustment screw 58 with a shaft turning in lower base portion 128 which includes the transverse channel for sliding base 122 and a radial sliding base extention 130 in turn mounted in a radial channel 132 of pipe positioning member 16.

Figure 6:
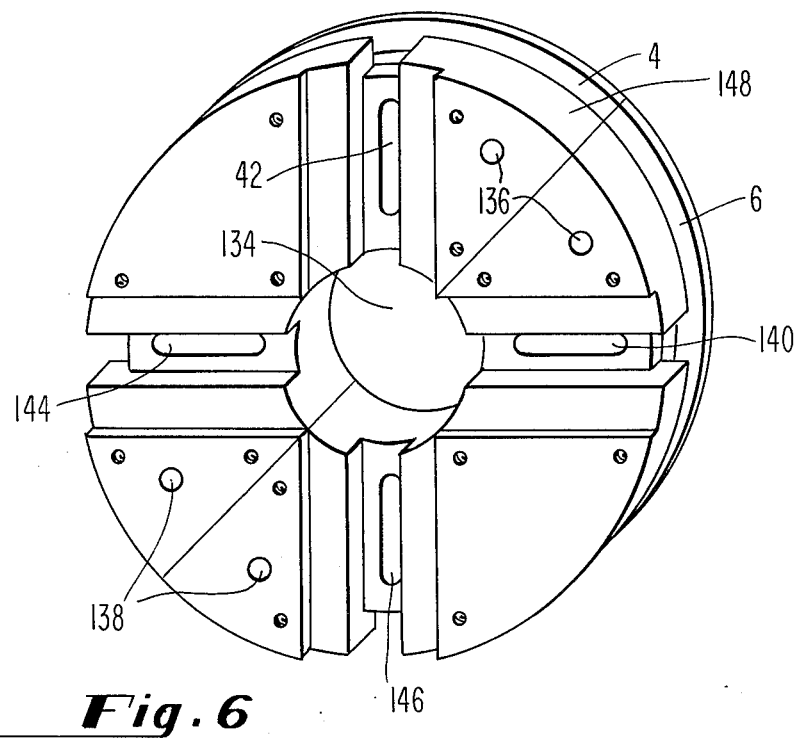
FIG. 6 is a perspective view of the base of the gauge shown in the previous figures.

Base sectors 4 and 6 of the base of gauge 2 are shown together in FIG. 6. The central axial opening 134 of the gauge base is there seen as well as hole pairs 136 and 138 for securing together base sectors 4 and 6. Also seen in FIG. 6 are slotted mounting holes 140, 142, 144 and 146. The pipe positioning members are mounted on the gauge base and bolts such as bolt 96 seen in FIG. 2, secure the pipe positioning members to the gauge base, the preselected pipe diameter being the determining factor in the position of the bolts in slots 140, 142, 144 and 146.

Gauge base sectors 4 and 6 together provide a cylindrical outer surface 148 for easy rotation of the gauge of this invention in gauge mount 80 and 82, seen in disassembled form in FIG. 7. In particular, gauge 2 fits within circular channel 150 in gauge mount 80 and 82 so that gauge 2 may be assembled about pipe 10 by first locating gauge base sector 6 and its associated mounts and rotating base sector 6 to the lower half of pipe 10 in gauge mount 82. Base sector 4 and its associated equipment is then assembled over pipe 10 and base sector 6 and secured thereto by means of fastening pins 11. Upper gauge mount 80 is then lowered over lower gauge mount 82 and secured by means of pins 84 (as seen in the cross-section detail view of FIG. 8) with projecting shafts 86 and 88. Retainer bolts 90 then complete the assembly. The gauge of this invention may include a single acoustic generator-sensor combination rather than four as in the embodiment illustrated in the figures. In either case, and particularly where a single generator-sensor is involved, it may be desirable to rotate the gauge during operation so as continuously to monitor wall thickness about the circumference of the pipe. The gauge of the present invention may thus be rotated by hand within channel 150 of the gauge mount seen in FIGS. 1 and 7. Alternatively, as shown in the form of the invention as seen in FIG. 9, the gauge base may be provided with associated gear teeth 152 meshing with a drive gear 154 in turn driven by a sprocket 156 and sprocket chain 158 turned by a crank 160 (shown in phantom in FIG. 9). Thus hand operation of crank 160 will serve to rotate a gauge associated with gear teeth 152 about a centrally located pipe 160 so that individual acoustic signal generator-receiver units are rotated for monitoring of different points about the periphery of pipe 160. Because of the associated electrical cables, the gauge would ordinarily not be rotated for more than 360° and usually would be limited to 180° of rotation.

In operation, the acoustic signal generator-sensor unit would be adjusted so as to produce a well-defined signal. Ordinarily, this occurs when the sensor is adjusted in a position so as to be aimed directly at axis 8 and perpendicularly thereto with the forward face of the sensor unit a preselected distance from the outer wall of the pipe to be gauged.

Acoustic signal generator-sensors of the type used in the present invention are well known and may be procured from any one of several commercial manufacturers. Such units depend on a medium, such as water, for transmitting the acoustic signals. These units therefore are well adapted for use in gauges of the present invention which are intended for the gauging of wall thickness of plastic pipe. Such pipe is usually extruded into a water bath. These gauges therefore permit the continuous gauging of all thicknesses of the pipe as it is extruded. The electronic signal based on the time delay between the reflected acoustic signal may be converted to a visual output which may be manually monitored. Alternatively, it may be converted into a high or low wall thickness indicator warning or may be fed to a proportional controller for affecting the pipe extrusion process, thereby automatically correcting any developing defect in wall thickness.

Although this invention has been described with respect to the use of a pipe 10, it will be appreciated that a special plug may be used, as shown in FIG. 10 of the drawings, to set and to center the jaws or the pipe positioning members such as pipe positioning member 16 and pipe positioning member 14 in centering the apparatus in preparation for production of pipe. The plug shown in FIG. 10 includes a large, generally cylindrical base 200 of a size for convenient gripping by hand, and a pipe blank 201 formed integrally therewith. The operator of the apparatus can, at any desired location remote from the pipe extruder or water bath, simply insert a portion 201 in the area normally occupied by the pipe 10, between the members 20, 22, 24 and 26, with the enlarged portion 200 snugly fitted against the backs of these members. In this way, exact preliminary centering is readily and conveniently achieved. The plug 201 can then be removed from the apparatus, and the apparatus is ready for the production of pipe having an outside diameter which corresponds exactly to the outside diameter of the cylindrical portion 201.

It will be clear, referring to FIG. 9, that it is readily possible to mechanize the member 160 so that a single measuring device, or plural measuring devices, may be driven in any cycle that is desired. For example, conventional circuits or timers may be used so that at a given time a continuous reading is taken 360° around the pipe, the rotation is then stopped by the timer and then after a predetermined period the mechanism is driven in reverse, either taking readings or not, and then a further dwell period may be provided by the timer, after which the entire measuring cycle may be repeated. In this manner, all readings may be recorded on a strip chart recorder, etc., or control signals can be sent to make any necessary adjustments, etc.

While the present invention has been described with respect to specific embodiments, it should be understood that this invention is not limited thereto. The appended claims are intended to be construed to cover all such equivalent modifications and variations which are within the true spirit and scope of the present invention.

What is claimed:

1. In a pipe wall thickness gauge including at least one wall thickness indicator consisting of an acoustic signal generator, a sensor for receiving reflected acoustic signals, a common generator-sensor housing and electronic time differentiation and indication means electrically connected to said generator and to said sensor for determining the time delay between two acoustic signal reflections from the inside and the outside of the wall of a pipe and converting said time delay into a signal proportional to the wall thickness of said pipe, the improvement comprising: a gauge base adapted to surround circumferentially a pipe located along the axis of said gauge, said base consisting of at least two separable sectors, each of which subtends an arc of no more than 180° around said axis, each of said sectors including at least one pipe positioning member with pipe centering elements at the tips thereof pointed radially inward toward said axis, all of said positioning and centering elements being adapted to maintain a pipe in a position along said axis, at least one of said pipe positioning members including means for holding said generator-sensor housing in a precisely predetermined position relative to a pipe maintained in a position along said axis by said positioning and centering elements, said generator-sensor housing holding means projecting from said pipe positioning member in a direction parallel to said axis, said holding means further including adjustment means for adjusting the position of said acoustic signal generator and said sensor relative to said pipe positioning member, in the radial direction, in the direction perpendicular to said radial direction in a plane perpendicular to said axis, and in angular inclination relative to a plane perpendicular to said axis, said generator-sensor holding means consisting of a generator-sensor housing retainer having flat side walls and adjacent flat surfaces forming an angle therewith, said retainer being enclosed by a holder having mating flat side walls, a pivotal attachment securing each of said holder side walls to said mating retainer side walls at a point, said generator-sensor housing being located between said pivotal attachment points, the opposite said holder side walls each including a threaded adjustment screw having a camming tip in contact with one of said inclined plane surfaces of said retainer, one of said screws being located closer to said axis and the other further away from said axis than the center of said generator-sensor housing.

* * * * *